(12) United States Patent
Todd

(10) Patent No.: US 8,910,630 B2
(45) Date of Patent: Dec. 16, 2014

(54) CANNABIS DRUG DELIVERY AND MONITORING SYSTEM

(75) Inventor: William W. Todd, Sea Cliff, NY (US)

(73) Assignee: PalliaTech, Inc., Sea Cliff, NY (US)

( * ) Notice: Subject to any disclaimer, the term of this patent is extended or adjusted under 35 U.S.C. 154(b) by 157 days.

(21) Appl. No.: 13/554,125

(22) Filed: Jul. 20, 2012

(65) Prior Publication Data

US 2012/0304990 A1 Dec. 6, 2012

Related U.S. Application Data

(63) Continuation of application No. 13/574,019, filed as application No. PCT/US2011/042255 on Jun. 28, 2011.

(60) Provisional application No. 61/359,161, filed on Jun. 28, 2010, provisional application No. 61/359,588, filed on Jun. 29, 2010, provisional application No. 61/373,333, filed on Aug. 13, 2010, provisional application No. 61/416,892, filed on Nov. 24, 2010.

(51) Int. Cl.
| | |
|---|---|
| *H05B 3/00* | (2006.01) |
| *F23D 14/00* | (2006.01) |
| *A61M 15/00* | (2006.01) |
| *A61M 16/00* | (2006.01) |
| *A61M 11/04* | (2006.01) |

(52) U.S. Cl.
CPC ......... *A61M 15/0028* (2013.01); *A61M 11/041* (2013.01); *A61M 11/042* (2014.02); *A61M 15/0081* (2014.02); *A61M 16/0063* (2014.02); *A61M 2205/276* (2013.01); *A61M 2205/3368* (2013.01); *A61M 2205/3553* (2013.01); *A61M 2205/3592* (2013.01); *A61M 2205/502* (2013.01); *A61M 2205/6009* (2013.01); *A61M 2205/6054* (2013.01); *A61M 2205/6072* (2013.01)
USPC ............ 128/203.27; 128/203.26; 128/203.14; 128/203.12

(58) Field of Classification Search
USPC ............. 128/204.17–204.21, 207.14, 202.21, 128/203.21, 203.26–203.27
See application file for complete search history.

(56) References Cited

U.S. PATENT DOCUMENTS

| | | |
|---|---|---|
| 3,392,902 A | 7/1968 | Donovan |
| 4,141,369 A | 2/1979 | Burruss |
| 5,284,133 A | 2/1994 | Burns et al. |
| 5,887,707 A | 3/1999 | Anascavage et al. |

(Continued)

FOREIGN PATENT DOCUMENTS

| | | |
|---|---|---|
| GB | 318214 | 1/1930 |
| WO | 2012/006125 A1 | 1/2012 |

OTHER PUBLICATIONS

International Search Report and Written Opinion for International Patent Application No. PCT/US2011/042255, dated Nov. 16, 2011.

(Continued)

*Primary Examiner* — Rachel Young
(74) *Attorney, Agent, or Firm* — Greenberg Traurig, LLP

(57) ABSTRACT

This invention relates to a new technology that enables administration of *Cannabis* to patients for medical purposes. In one embodiment, this invention is a component of a system of technologies, processes and concepts that creates a new method of producing, delivering, administering and regulating the use of medical *cannabis*.

17 Claims, 13 Drawing Sheets

(56) References Cited

U.S. PATENT DOCUMENTS

| | | |
|---|---|---|
| 6,003,006 A | 12/1999 | Colella et al. |
| 6,021,392 A | 2/2000 | Lester et al. |
| 6,095,153 A * | 8/2000 | Kessler et al. ............... 131/194 |
| 6,513,524 B1 | 2/2003 | Storz |
| 6,761,164 B2 | 7/2004 | Amirpour et al. |
| 6,990,978 B2 | 1/2006 | Shayan |
| 7,088,914 B2 | 8/2006 | Whittle et al. |
| 7,186,958 B1 | 3/2007 | Nelson |
| 7,278,427 B2 | 10/2007 | Cheng |
| 7,445,007 B2 | 11/2008 | Balch et al. |
| 7,624,734 B2 | 12/2009 | Balch et al. |
| 2002/0087360 A1 | 7/2002 | Pettit |
| 2002/0087362 A1 | 7/2002 | Cobb et al. |
| 2003/0217750 A1 | 11/2003 | Amirpour et al. |
| 2004/0217024 A1 | 11/2004 | Arnarp et al. |
| 2004/0258622 A1 | 12/2004 | Peart et al. |
| 2005/0123635 A1 | 6/2005 | McAughey et al. |
| 2005/0279353 A1 | 12/2005 | McCoy |
| 2006/0062734 A1 | 3/2006 | Melker et al. |
| 2006/0130829 A1 * | 6/2006 | Sexton et al. ............. 128/200.23 |
| 2006/0237002 A1 * | 10/2006 | Bonney et al. ............ 128/200.23 |
| 2007/0045288 A1 * | 3/2007 | Nelson ........................ 219/533 |
| 2007/0240715 A1 | 10/2007 | Hill |
| 2008/0029099 A1 | 2/2008 | Storz |
| 2008/0078382 A1 | 4/2008 | LeMahieu et al. |
| 2008/0095278 A1 | 4/2008 | Li et al. |
| 2009/0007904 A1 | 1/2009 | Schuster et al. |
| 2009/0024112 A1 | 1/2009 | Edwards et al. |
| 2009/0071475 A1 | 3/2009 | Fishman |
| 2009/0293888 A1 * | 12/2009 | Williams et al. .............. 131/178 |
| 2009/0314292 A1 * | 12/2009 | Overfield et al. ........ 128/203.15 |
| 2010/0012118 A1 * | 1/2010 | Storz ........................ 128/203.15 |
| 2010/0158973 A1 | 6/2010 | Weiss et al. |

OTHER PUBLICATIONS

International Search Report and Written Opinion for International Patent Application No. PCT/US2011/042254, dated Nov. 9, 2011.

* cited by examiner

CANNABIS DRUG DELIVERY AND MONITORING SYSTEM

CROSS-REFERENCE TO RELATED APPLICATIONS

This application is a continuation of prior U.S. application Ser. No. 13/574,019 filed Jul. 19, 2012, which is a §371 national stage application of and claims priority to International Application No. PCT/US2011/042255 filed on Jun. 28, 2011, and which also claims priority to each of U.S. Provisional Patent Applications Nos. 61/359,161, filed Jun. 28, 2010; 61/359,588, filed Jun. 29, 2010; 61/373,333, filed Aug. 13, 2010; and 61/416,892, filed Nov. 24, 2010, each of the aforesaid applications being incorporated by reference herein in their entireties for all purposes.

BACKGROUND OF THE INVENTION

The palliative effects of certain vaporizable substances (for example, *Cannabis*), have been recognized. For example, *Cannabis* may be utilized to ameliorate symptoms of debilitating diseases and conditions, including, but not limited to, arthritis; cancer; AIDS; Crohn's disease; chronic pain; epilepsy; glaucoma; migraine headaches; multiple sclerosis; and/or sever muscle spasms.

BRIEF DESCRIPTION OF THE INVENTION

In one embodiment, a method comprising:
A. obtaining a purpose-built medical inhalation device;
B. obtaining at least one authorized dosage form of medical *Cannabis*;
C. inserting the authorized dosage form into the purpose-built medical inhalation device;
D. unlocking use of the purpose-built medical inhalation device for a single dose cycle;
E. delivering a dose of medical *Cannabis* to the patient utilizing the unlocked medical inhalation device in combination with the inserted dosage form; and
F. recording consumption data relating to the use of the device and/or dosage form.

In another embodiment, further comprising the step of verifying that a patient is authorized to use the inserted dosage form with the purpose-built medical inhalation device;

In another embodiment, wherein the purpose-built medical inhalation device is for the delivery of medical *Cannabis*.

In another embodiment, wherein the verifying step comprises identifying a patient with a prescription.

In another embodiment, wherein the verifying step comprises confirming that a patient is legally qualified for use of medical *Cannabis*.

In another embodiment, wherein the verifying step comprises confirming that a dosage form is legally qualified for use with the purpose-built medical inhalation device.

In another embodiment, wherein the verifying step comprises confirming that the purpose-built medical inhalation device is authorized for use at a particular location.

In another embodiment, wherein the verifying step comprises that the dosage form is authorized for use at a particular location.

In another embodiment, wherein the purpose-built medical inhalation device delivers a dose of medical *Cannabis* without combustion.

In another embodiment, wherein the verifying step comprises biometrically identifying a patient.

In another embodiment, wherein the delivered dose is sanitary.

In another embodiment, wherein the delivered dose is sterile.

In another embodiment, further comprising the step of locking out the device when the frequency of use of the machine exceeds a given set point.

In another embodiment, further comprising the step of reporting consumption data to a patient's medical services provider.

In another embodiment, further comprising the step of locking out the device when the identity of the user of the machine does not match the patient authorized to use the dosage form.

In another embodiment, further comprising the step of locking out the device when an inserted dosage form is not authorized for use with the purpose-built medical inhalation device.

In another embodiment, further comprising the step of locking out the device when the biometric identification of a user does not match the identity of an inserted dose form.

In another embodiment, wherein the dosage form is tamper-evident.

In another embodiment, further comprising the step of locking out the device when the inserted dosage form has been tampered with.

In another embodiment, wherein the recording step comprises recording time and location of unlocking of the device.

In another embodiment, wherein the dose of medical *Cannabis* is delivered via a cannula.

In another embodiment, wherein the delivery temperature of the dose of medical *Cannabis* does not exceed the heat of combustion of the dose.

In another embodiment, a tamper-evident dosage form comprising a sterile, measured dose of medical *Cannabis*.

In another embodiment, wherein the dosage form is not accessible until biometric authorization is obtained.

In another embodiment, wherein the dosage form is not accessible until availability of the dose is verified.

In another embodiment, a medical inhalation system for delivery of inhaled medical *Cannabis* to a patient, comprising:
a. a medical inhalation device for the delivery of medical *Cannabis*;
b. a tamper-evident dosage form comprising a sterile, measured dose of medical *Cannabis*,
c. an insertion chamber designed for selective acceptance of the dosage form into the medical inhalation device;
d. a control system for verifying authorized use of the dosage form in the medical inhalation device by a patient, comprised of a control system that unlocks the medical inhalation device for delivery of the dosage form upon verification of the authorized use; and
e. a recording system for recording dosage form and medical device usage data.

In another embodiment, wherein the control system queries a database to match the dosage form with the patient.

In another embodiment, wherein the control system queries a database to match the dosage form with usage data.

In another embodiment, wherein the control system queries a database to match the dosage form with a prescribed user.

In another embodiment, wherein the control system queries a database to confirm that a dosage form is legally qualified for use with the purpose-built medical inhalation device.

In another embodiment, wherein the control system locks out the device when the frequency of use of the machine exceeds a given set point.

In another embodiment, wherein the control system reports consumption data to a patient's medical services provider.

In another embodiment, wherein the control system is capable of reporting consumption data to a patient's medical services provider.

In another embodiment, wherein the control system is capable of locking out the device when an inserted dosage form is not authorized for use with the purpose-built medical inhalation device.

In another embodiment, wherein the control system is capable of locking out the device when the biometric identification of a user does not match the identity of an inserted dose form.

In another embodiment, wherein the control system is capable of locking out the device when the biometric identification of a user does not match the identity of an inserted dose form.

In another embodiment, further including a biometric identification device.

In another embodiment, further including a cannula.

In one embodiment, the invention is a device designed to administer medical *Cannabis* in consistent, single doses and with a degree of safety and control.

In one embodiment, the instant invention encompasses proprietary medical dose delivery and monitoring systems that address health, safety, public safety, and law enforcement issues with respect to the emerging medical *cannabis* industry.

In one embodiment, the device administers medical *cannabis* via vaporization by accommodating measured, pre-packaged doses and placing them precisely in a specially-designed vaporization chamber to enable a physician-recommended course of therapy. Doses are heated precisely to a temperature that produces therapeutically-active cannabinoid vapors (approximately 180-190° C.) but below the point of combustion (approximately 230° C.) that produces noxious byproducts, particularly carcinogenic polynuclear aromatic hydrocarbons (PAHs) which are believed to be a major cause of smoking-related cancers. In one embodiment, drug delivery is safer (without noxious byproducts of combustion); consistent (dose-to-dose); reproducible (by standardizing the mechanics of delivering a standard dose of active ingredient via vaporization stream); and easier to administer to a variety of patients with varying functionalities.

In one embodiment, the device administers medical *cannabis* via vaporization by accommodating measured, pre-packaged doses and placing them precisely in a specially-designed vaporization chamber to enable a physician-recommended course of therapy. The vaporization chamber may optionally include some combination of baffles; intake restriction; and/or heat or dose size limitations that will prevent combustion of the medical dose on administration to the patient, without substantial variance as to combustion/substances delivered to patient as a function of the patient's lung capacity and/or strength of inhale.

In another embodiment, the invention is also purpose-built to collect critical clinical and product-tracking data including time, date and number of doses administered. By recording data, the device enables analysis and control of usage by authorized parties e.g., physicians and state regulators. In one embodiment, the dose vaporization chamber accepts and positions the pre-packaged dose for optimal vaporization, and the complementary installed microprocessor/software module is configured to collect data and to interface with HIPAA-compliant data management and regulatory reporting systems.

In one embodiment, the instant invention introduces distinct, commercially-valuable advantages for patients, their primary care-givers, physicians, regulators and the industry as a whole. Patients enjoy ease-of-use (particularly important for the chronically ill), a safe and healthier alternative to smoking and a precise, consistent method of administering medical *cannabis* for maximum therapeutic benefits.

In another embodiment, the instant invention produces a mild, non-irritating and non-noxious vapor, allowing the use of inhalation, the method of administration preferred by most patients. By precisely placing the dose in the vaporization chamber, the device enables highly efficient vaporization, which allows direct, improved absorption of active ingredients (increased therapeutic efficacy) and reduces waste (saves money). In many of these respects, the instant invention dose vaporizer also has significant potential commercial value as a new device in jurisdictions that have legalized *Cannabis* for recreational use.

In another embodiment, the instant invention permits physicians to record and control frequency, time and date of use while enabling treatment to the dose-response curve of individual patients (a critical healthcare benefit). Doctors can deliver improved care due to the patient's ability to self-administer consistent doses. Tamper-resistant packaging and digital record-keeping offer states and law enforcement authorities new tools to help ensure accountability, control and transparency throughout the medical *Cannabis* supply chain.

In another embodiment, the instant invention delivers a product that is processed and packaged for consistency, efficacy and single-dose use. The Dose Vaporizer serves a new market category of premium-priced *Cannabis* products formulated for medicinal purposes with hardware, software, features and esthetics uniquely suited to non-recreational, medicinal uses.

In another embodiment, the vapor is delivered into the patient's lungs via mouth or nose propelled by the patients inhalation or an automatic fan, blower, or other propulsion means.

In another embodiment, the instant invention relates to allowing society a machine that cannot be utilized or reconfigured to use a medical substance in a way that is not intended and is currently illegal relieving law enforcement and society the burden of having to monitor medical marijuana with more resources.

BRIEF DESCRIPTION OF THE SEVERAL VIEWS OF THE DRAWINGS

The present invention will be further explained with reference to the attached drawings, wherein like structures are referred to by like numerals throughout the several views. The drawings shown are not necessarily to scale, with emphasis instead generally being placed upon illustrating the principles of the present invention.

Figure 1:
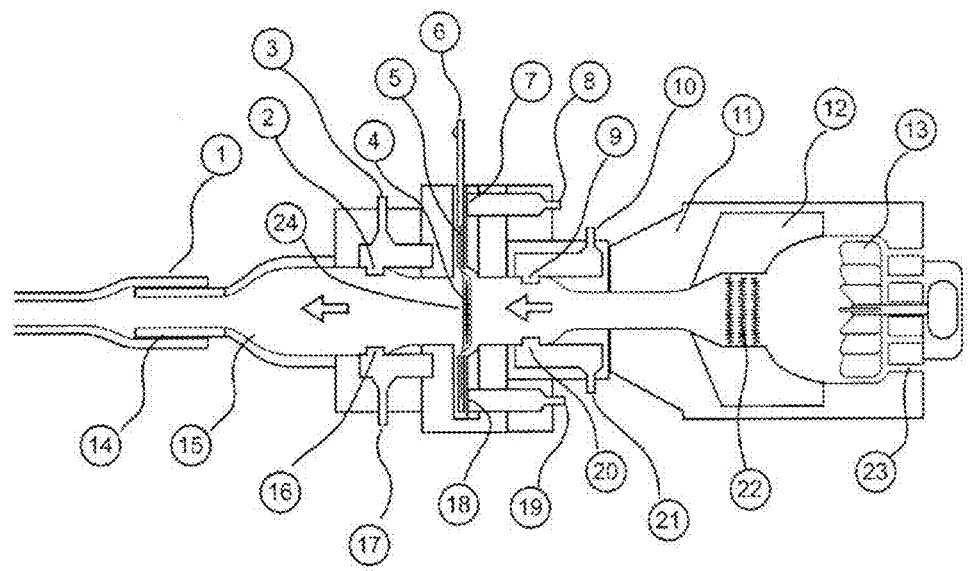
FIG. 1 depicts an embodiment of a medical dose vaporizer and cartridge.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed invention.

DETAILED DESCRIPTION OF THE INVENTION

Detailed embodiments of the present invention are disclosed herein; however, it is to be understood that the disclosed embodiments are merely illustrative of the invention that may be embodied in various forms. In addition, each of the examples given in connection with the various embodiments of the invention are intended to be illustrative, and not restrictive. Further, the figures are not necessarily to scale, some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

The term "purpose-built medical inhalation device" means: a device designed and manufactured for medical use as a method of administering therapeutic doses of *Cannabis* in the form of an inhaled vapor.

The term "medical *Cannabis*" means: a form of the plant genus *Cannabis*, in the form of ground plant material comprising bud, leaf, and stem materials of the *Cannabis* genus, or any combination thereof.

The term "authorized" means: an individual or use that is approved for a medical *Cannabis* therapy by a recommending physician or other legally or administratively authorized provider.

The term "measured" means: marked by due proportion or precise weights and measures.

The term "sterile" means: treated with any of a number of recognized sterilization methods that leave the sample free from living organisms and especially microorganisms.

The term "sanitary" means: free from living, esp pathogenic, microorganisms, and detrius associated therewith, for example insect parts, spores, etc.

The term "sterilizable" means: capable of being rendered sterile multiple times.

The term "tamper-evident" means: a form of packaging or presentation that renders improper and unauthorized use obvious to inspection (for example, visual, machine, or electronic inspection).

The term "dosage form" means: a formulation that presents or administers a medicine or therapy in a single, measured, clinically-appropriate unit.

The term "verifying" means: to confirm proper or authorized use or identification.

The term "patient" means: an individual awaiting or under medical care and treatment.

The term "unlocking" means: to open for use or access.

The term "single dose cycle" means: the time and steps required to administer one dose of medicine.

The term "delivering" means: to bring or transport to the proper place or recipient; to distribute or administer.

The term "recording" means: the act or process of making a record; a record.

The term "wherein the patient is identified with a prescription" means: pertaining to a patient who has received a prescription or recommendation from a qualified physician.

The term "biometrically identified" means: the verification of identity via physical characteristics, such as fingerprints, DNA, or retinal patterns.

The term "prescription" means: A written order, especially by a physician, for the preparation and administration of a medicine or other treatment; a recommendation of a medicine or other treatment from a physician.

The term "without combustion" means: with no burning; the absence of fire, smoke and the byproducts of burning. With respect to medical *Cannabis*, "without combustion" means heating *cannabis* to a *Cannabis* material temperature of between 180 and 200 C, thereby vaporizing the cannabinoids that reside on the trichomes on the surface of *cannabis* flowers and leaves, while avoiding combustion (which occurs at 230 C and above) and attendant smoke toxins.

The term "locking out" means: denying access; disabling a mechanism or feature; prohibiting an activity.

The term "frequency of use of the machine" means: the number of times the device is used; the intensity of usage.

The term "exceeds a given set point" means: anything that surpasses a predetermined limit or benchmark.

The term "has been tampered with" means: has been subject to improper or unauthorized use; evidencing damage to the form of packaging or presentation.

The term "the delivery temperature of the dose of medical *Cannabis*" means: the temperature at which a single unit of *Cannabis*-based therapy is administered to a patient.

The term "the dosage form is not accessible until biometric authorization is obtained" means: the single unit of therapy is not available for administration without physical verification of identity or authorization.

The term "selective acceptance of the dosage form into the medical inhalation device" means: accommodating insertion of a unit of therapy only in a pre-determined manner.

The term "disposable" means: designed to be replaced and discarded after use.

The term "heat of combustion" means: The heat at which combustion occurs for a given substance—for example, approximately 230 C and above for medical *Cannabis*.

The term "availability of the dose is confirmed" means that a database or other verifying means confirms that a particular purpose-built machine/person is authorized to utilize a dose.

The term "one-way sanitary vapor valve" means: a valve that only allows the flow of vapor in a single direction.

The term "consumption data" means data related to the location, use, frequency of use, identity of user, and identity of product used with respect to a purpose-built vaporizer/dose combination "Legally qualified for use" means that a given purpose-built vaporizer/dosage form/individual is authorized for use or using a given medical *Cannabis* dose.

FIG. 1 depicts an embodiment of a medical *Cannabis* vaporizer and recording system. Removable vaporizer tube 1 is in communication with outflow vapor source 14 which receives vapor from the stabilizing chamber 15. Vapor flow is in the direction of the arrows indicated. Exhaust temperature and data sensors 2, 16, measure the temperature and other physical/chemical characteristics of the vapor. This data is optionally transmitted to exhaust sensor data connections 3, 17. The vapor itself is generated from heated air originating from intake ports 23, heated by a heating element 12, and passing through a medical dose 4 of a vaporizable substance (in one embodiment, *Cannabis*) held in place and surrounded by a dose suspension screen 5 itself contained within a medical dose cartridge 6. Vapor collects in the dose vaporizing chamber 24. Data recognition means (in one embodiment, an infrared-scannable barcode 7) may be located on the medical dose cartridge 6 so as to tracking and/or verifying use and user of the medical dose 4 through a dose-recognition switch 18, and may, in one embodiment, be readable by medical dose/data connections 8, 19. Separate intake temperature sensor data recorders 9 and data connections 10 may also be utilized. An insulation heat sink 11 absorbs excess heat and keeps the starting temperature of the heated air utilized to generate the vapor fairly constant. An intake temperature sensor and data recorder 20 associated with an intake temperature measuring device monitors the temperature of the heated air utilized to generate the vapor. In one embodiment, the air may itself be heated by a heat element 22 and driven through the machine by an air flow fan 13.

Figure 1A:
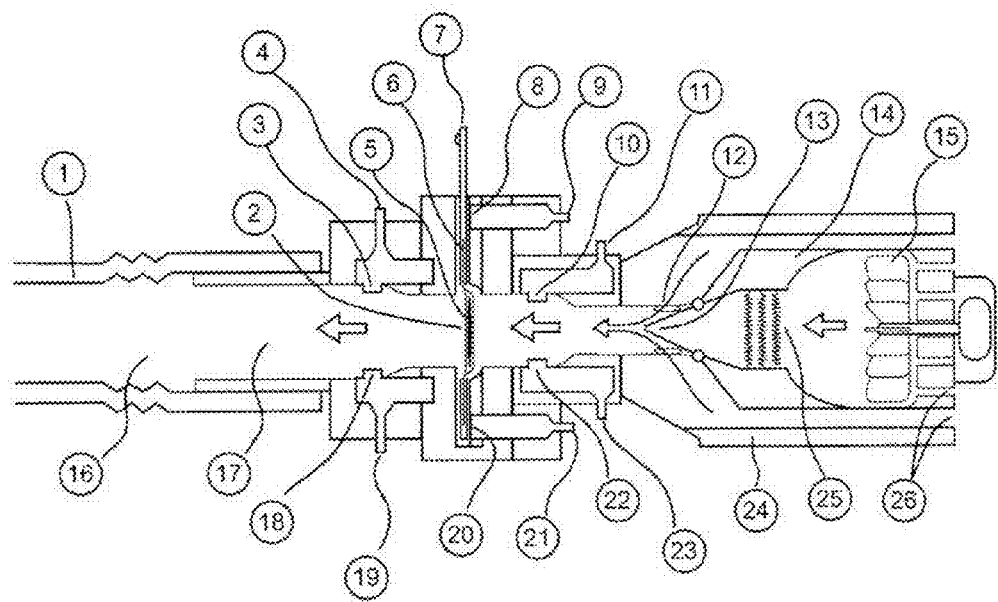
FIG. 1A depicts an embodiment of a medical dose vaporization chamber, cartridge and hot air flow restriction baffle.

FIG. 1A depicts an embodiment of a dose vaporizer similar to that shown in FIG. 1, with the added differences of a hot air flow restriction baffle 13, and air flow carburetor holes 12.

In another embodiment, the dose vaporizing chamber 6 is removable and/or separately packaged and salable, and can be attached and used with any other commercially available vaporizer and/or heat source by use of an adapter.

Figure 2:
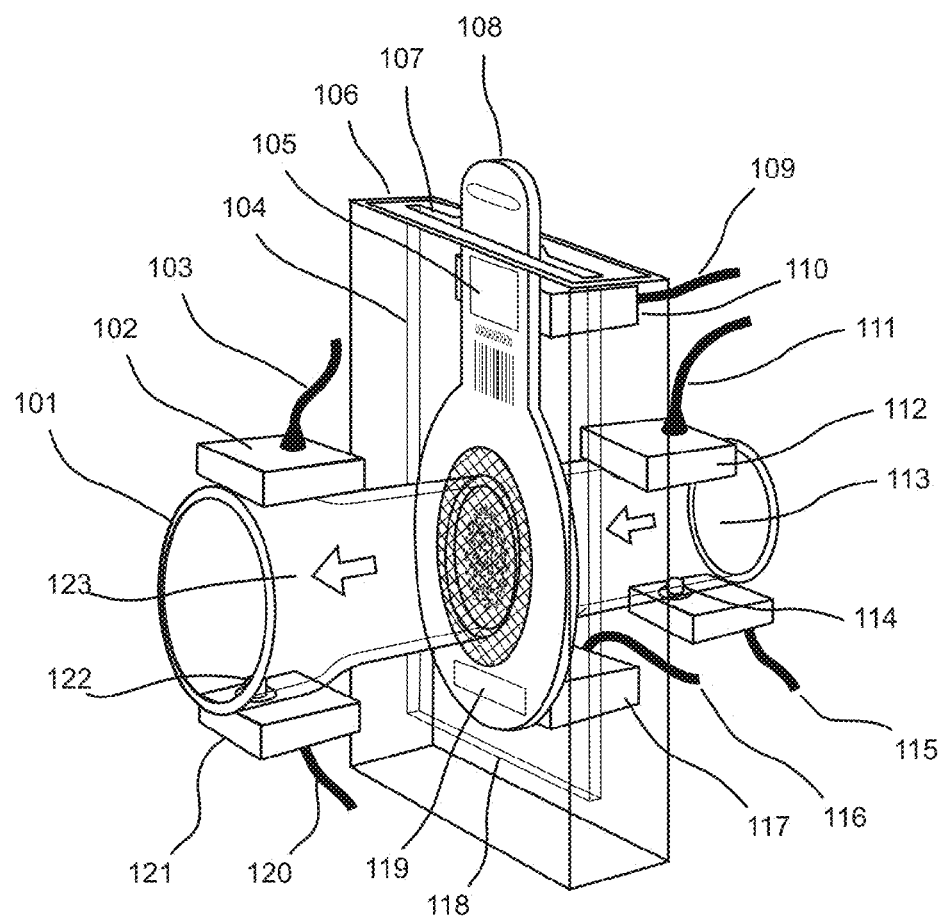
FIG. 2 depicts an embodiment of a medical dose vaporization chamber and cartridge.

FIG. 2 depicts an embodiment of the invention with a dose cartridge inserted. In one embodiment, the dose cartridge 108 includes a medical dose of a material between two metal screens that has not been previously vaporized or subject to other extraction or processing steps. Dose cartridge data 105 may, in one embodiment, be imprinted on the dose cartridge 108. The dose cartridge slot 104 holds a dosage cartridge 108 so that its wire mesh section is held within the dosage cartridge vaporizing chamber 106. Temperature regulated airflow 113 flows through the dosage, and its presence is measured utilizing a vapor temperature sensor 122. Vapor flows in the direction of the arrows shown 123. Vapor temperature sensor, data recording, and data connection means 102, 103, 120, 121 measure vapor temperature and chemical characteristics, while—upstream of the medical dose—temperature sensor, data recording and data connection means 111, 112, 114, 115 measure the temperature and/or other characteristics of the incoming air stream. The medical dose recognition switch 117 optionally allows operation of the machine only when an authorized dose/dose size is placed in the apparatus, and an optional data connection 116 allows connection to an outside computer and/or outside entity. Similar structures are provided at 109, 110.

Figure 3:
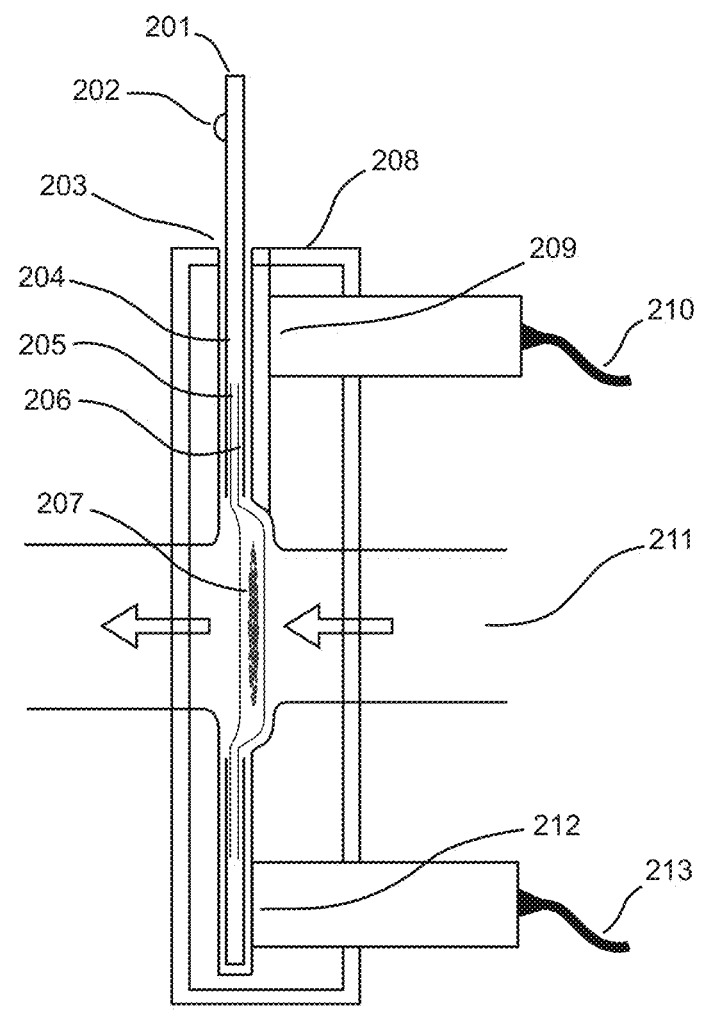
FIG. 3 depicts an embodiment of a dose cartridge, dose cartridge slot and dose vaporization chamber.

FIG. 3 is a side view of an embodiment of the dose cartridge, dose cartridge slot and dose vaporization chamber of the instant invention. The medical dose cartridge 201 includes a finger grip 202 for easy insertion and removal. The vaporization chamber slot 203 may be optionally designed so as only to accept a medical dose cartridge 204 of a particular configuration—thus "locking out" use of the apparatus to any potential user not utilizing a particularly configured medical dose cartridge. The cartridge is comprised of micro screens 205, 206 which hold a dose within the dose vaporization chamber 207. Cartridge and medical dose recognition and data connection means 209-210 and 212-213 optionally provide a mechanism to ensure that only a pre-approved, pre-measured particular dose of a medical herb or other substance is administered by matching the dose and cartridge identifying information.

Figure 4:
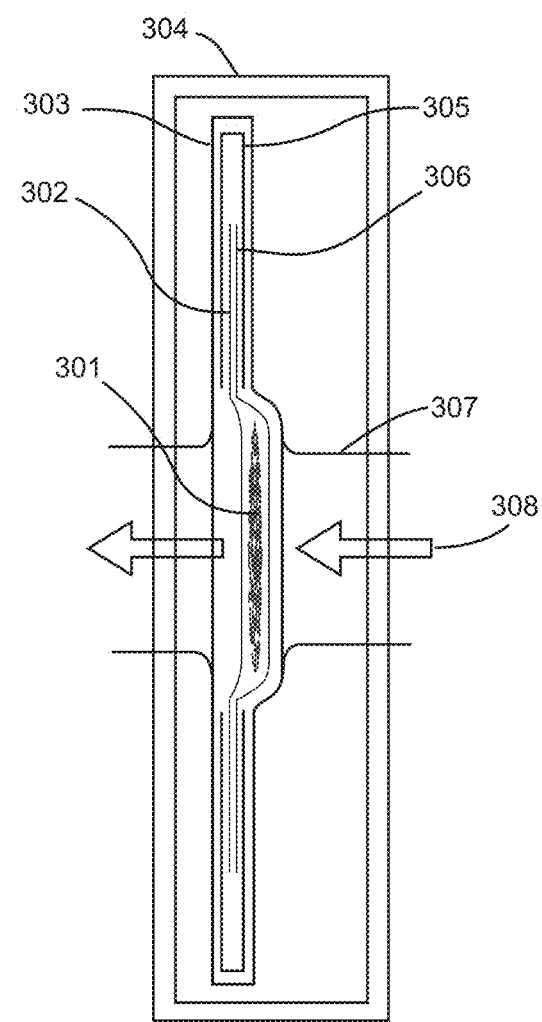
FIG. 4 depicts an embodiment of a dose cartridge, dose cartridge slot and dose vaporization chamber.

FIG. 4 is a top view of an embodiment of the dose cartridge, dose cartridge slot and dose vaporization chamber of the instant invention. The medical dose 301 is placed between microscreen layers 302, 306. The vaporization chamber slot 303 may be optionally designed so as only to accept a medical dose cartridge of a particular configuration—thus "locking out" use of the apparatus to any potential user not utilizing a particularly configured medical dose cartridge. The dose is positioned within a temperature regulated air flow 308 passing through an air flow hole 307 so as to ensure optimum efficiency in vaporization of the medical dose.

Figure 5A:
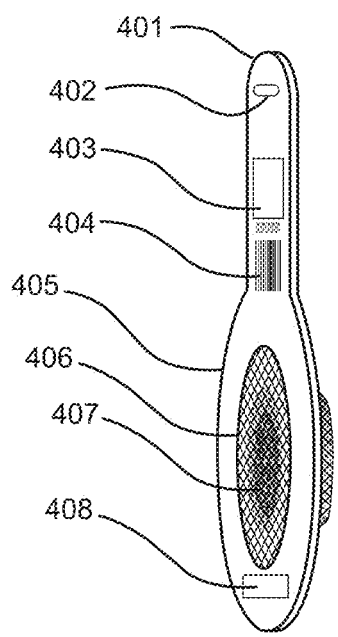
FIGS. 5A and 5B depicts an embodiment of a medical dose vaporization cartridge.
Figure 5B:
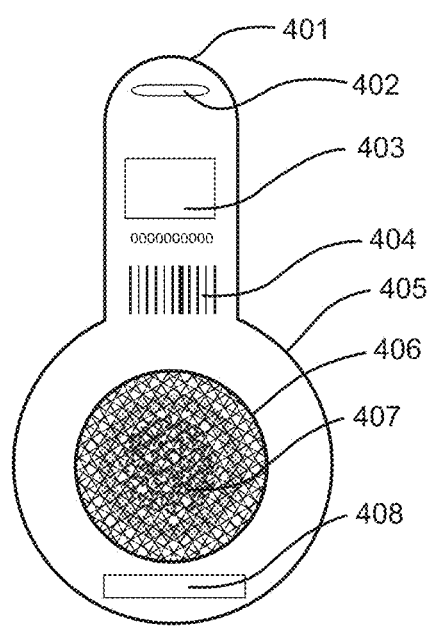

FIGS. 5A and 5B depicts an embodiment of the medical dose vaporization cartridge itself. The dose cartridge 401 includes a finger grip 402 and may optionally include a means for storing/transmitting product and/or cartridge specific data 403. An optional bar code 404 provides an additional means for identification/tracking. The dose housing 405, in one embodiment, wholly encapsulates a medical 407 dose between two screens 406 in a manner that allows for placement of a dose that is small enough to essentially prevent combustion; and thin and/or well-distributed enough to ensure consistent vaporization of relevant dose components throughout the vaporization process. A recognition switch 408 individually identifies the dose.

Figure 6A:
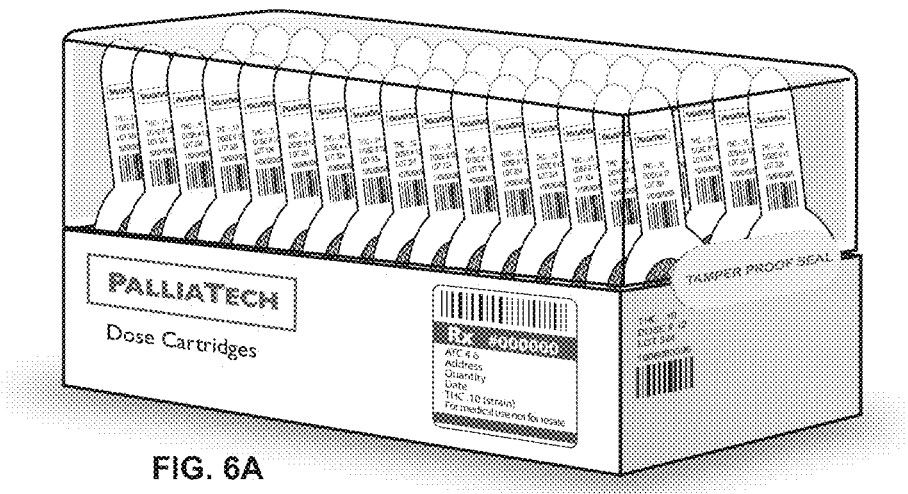
FIGS. 6A, 6B and 6C depicts an embodiment of a consumer packaging.
Figures 6B, 6C:
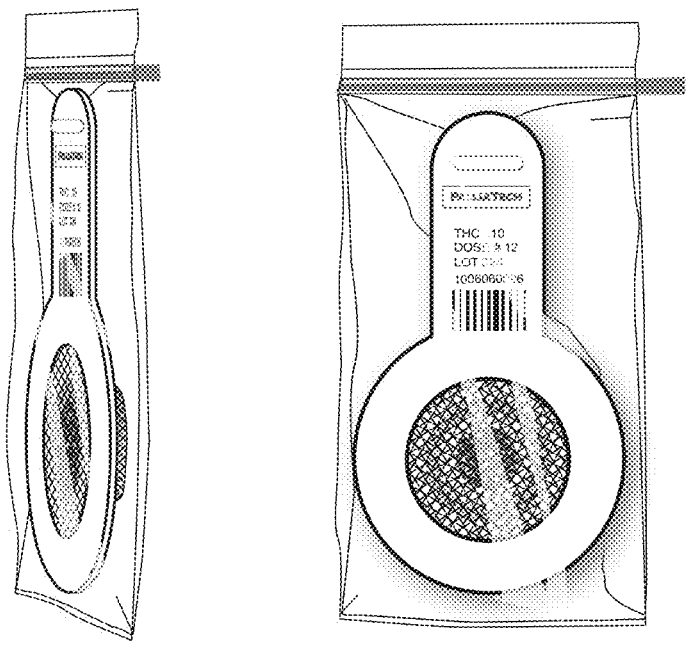

FIGS. 6A, 6B, and 6C depict an embodiment of consumer packaging utilized for the medical dose vaporization cartridges of the instant invention. In one embodiment, a plurality of cartridges are stored in a sterile airtight box. In another embodiment, the plurality of cartridges within the sterile airtight box are individually wrapped so as to ensure sterility when the box is repeatedly opened for dose access. In another embodiment, the consumer packaging is equipped with monitoring means so as, for example, to monitor the rate at which individual dose cartridges are removed from the box; the total number of cartridges removed from the box; and whether any dose cartridges removed and/or replaced within the box maintain sterility and/or are in a pre-vaporization state. In one embodiment, both the box and the individual cartridges may have individual monitoring and/or tracking means, including but not limited to computer chip, barcode and/or radiofrequency identification (RFID) tracking/monitoring/data transmission means.

Figure 7:
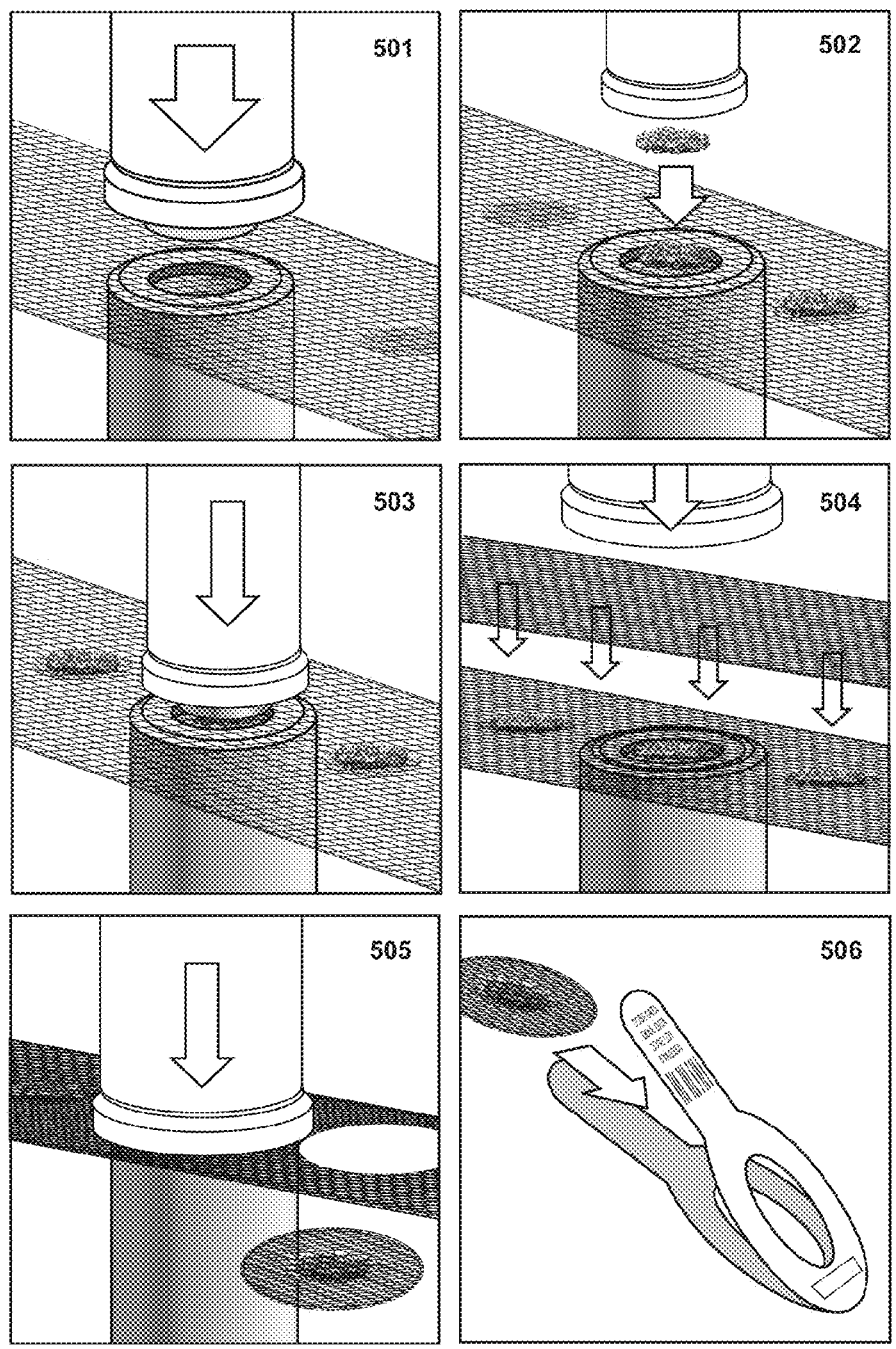
FIG. 7 depicts an embodiment of a dose cartridge assembly process.

FIG. 7 depicts an embodiment of a *Cannabis* dose cartridge assembly process. In one embodiment, this assembly process is carried out by the commercial provider of the medical dose. In another embodiment, this assembly process is carried out by a licensed physician/nurse/pharmacist or other authorized third party. In one embodiment, a screen is forged 501, so as to create a depression in the screen. The medical dose is placed 502 in the screen depression, and optionally tamped down 503. The medical dose is then encapsulated between screens 504. Once the dose is encapsulated between screens, the encapsulated dose may then be cut out 505 and inserted into a dose cartridge for commercial use 506.

Figure 8A:
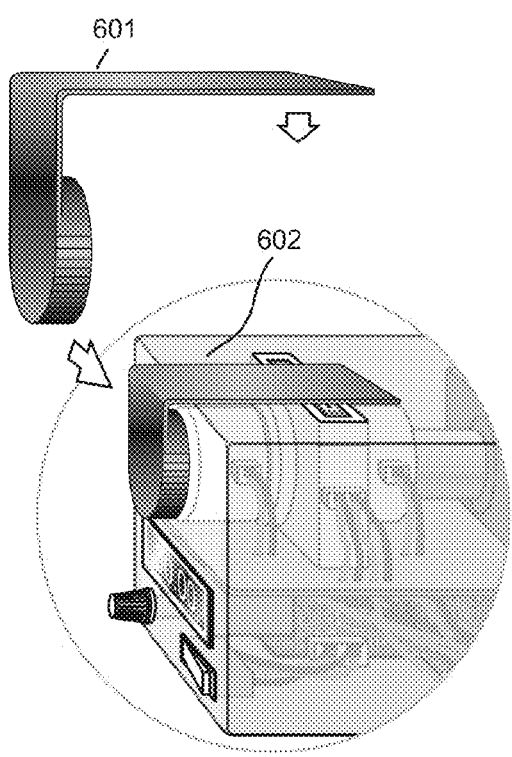
FIG. 8A and 8B depicts an embodiment of a maintenance and sterilization kit.
Figure 8B:
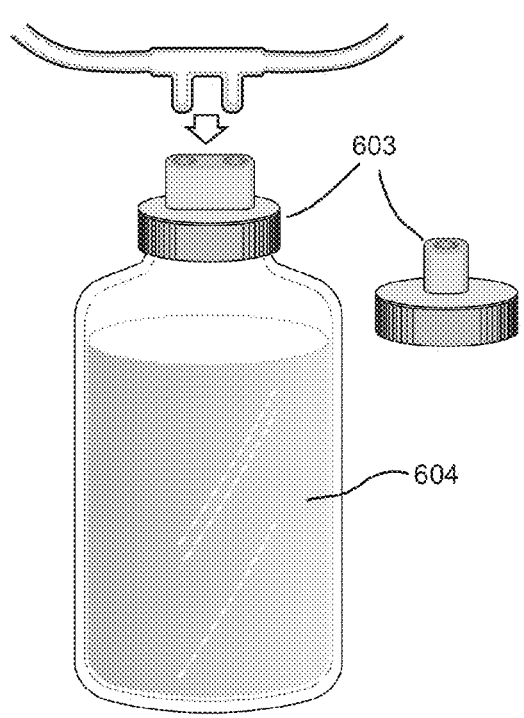

FIGS. 8A and 8B depict an embodiment of a maintenance and sterilization kit for use with the dose vaporizer of the instant invention. A heat shield sterilization safety cap 601 may be placed over the openings of the vaporization chamber 602 to prevent contamination between uses. Means for flushing the system are also provided 604.

Figure 9:
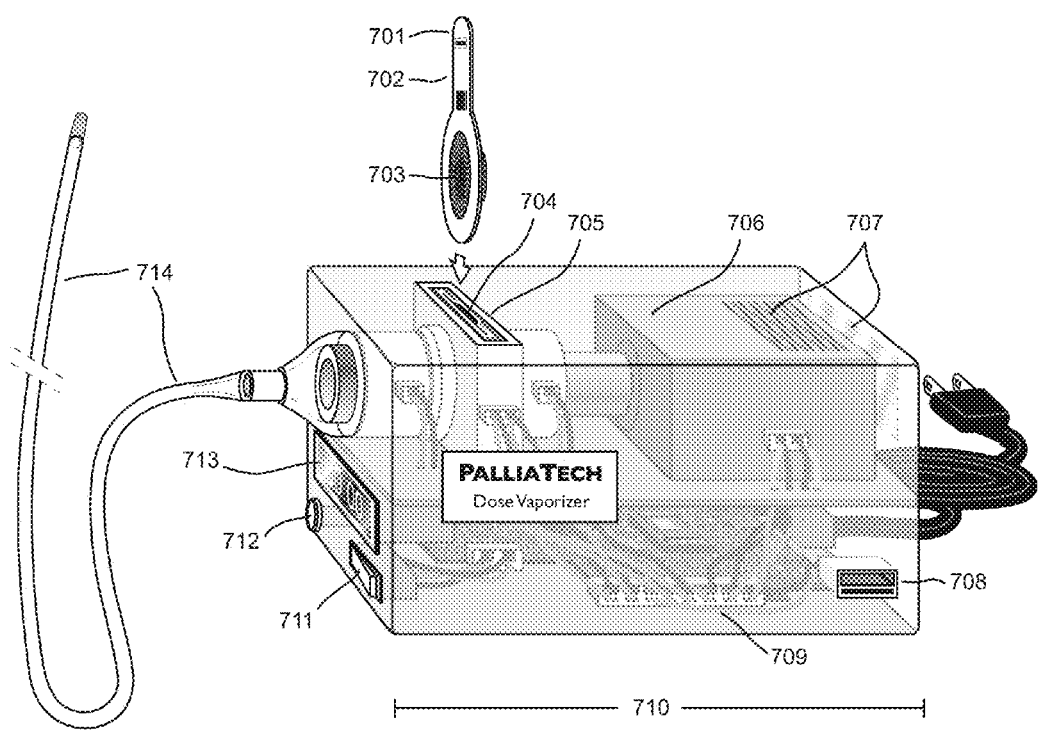
FIG. 9 depicts an embodiment of a dose vaporizer.

FIG. 9 depicts an embodiment of a dose vaporizer of the instant invention. An on/off switch 711 governs provision of power to the unit. Visual and digital data may be displayed, and a maintenance control 712 is also provided for optional control of vaporization parameters. A dose cartridge slot 704 is configured to only accept a particularly configured (physically and/or electronically or informationally) dose cartridge, and is further configured so as to place the medical dose contained within the dose cartridge in optimal contact with the heated air coming from the heat source so as to create a vapor stream. A dose location 703 is configured so as to maximize efficiency and efficacy of dose vaporization. A control data collection system 709 and USB data port(s) 708 permit recordation and/or monitoring of dose vaporizer utilization.

Figure 10:
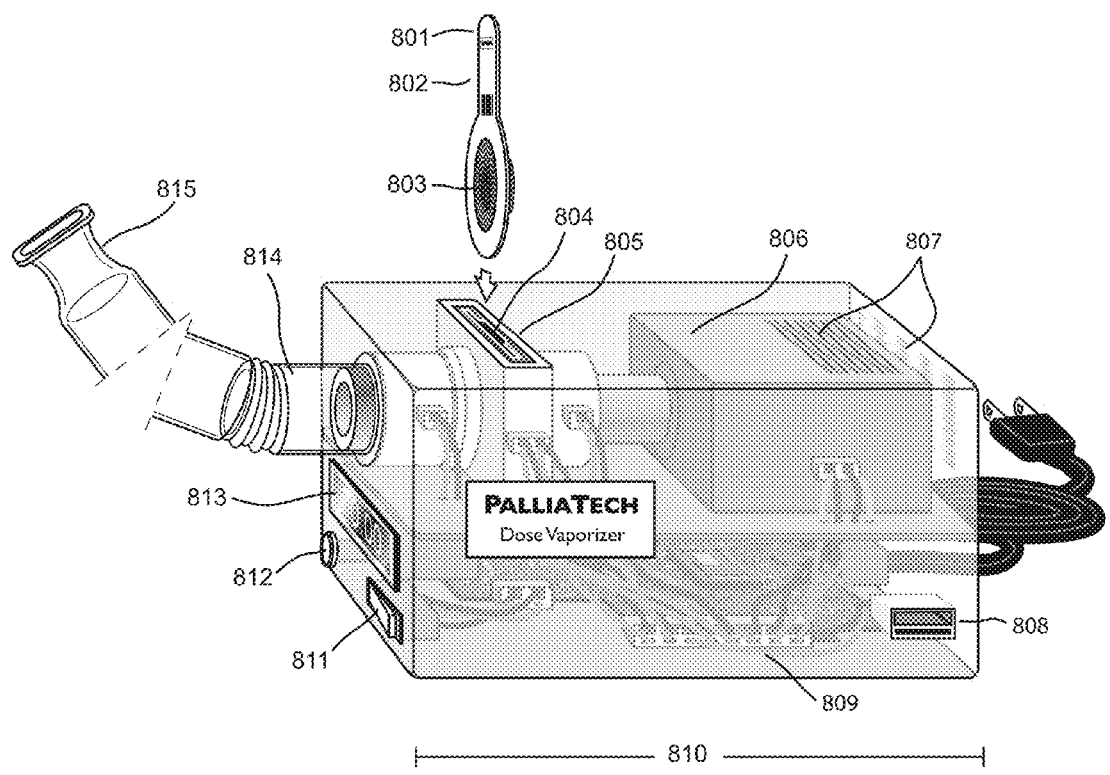
FIG. 10 depicts an embodiment of a dose vaporizer.

FIG. 10 is a variant of the dose vaporizer of FIG. 9, wherein the flexible tube 814 and mouthpiece 815 are differently configured. In one embodiment, the flexible tube and mouthpiece of FIG. 10 have an internal diameter substantially similar to that of the dose vaporization chamber.

Figure 11:
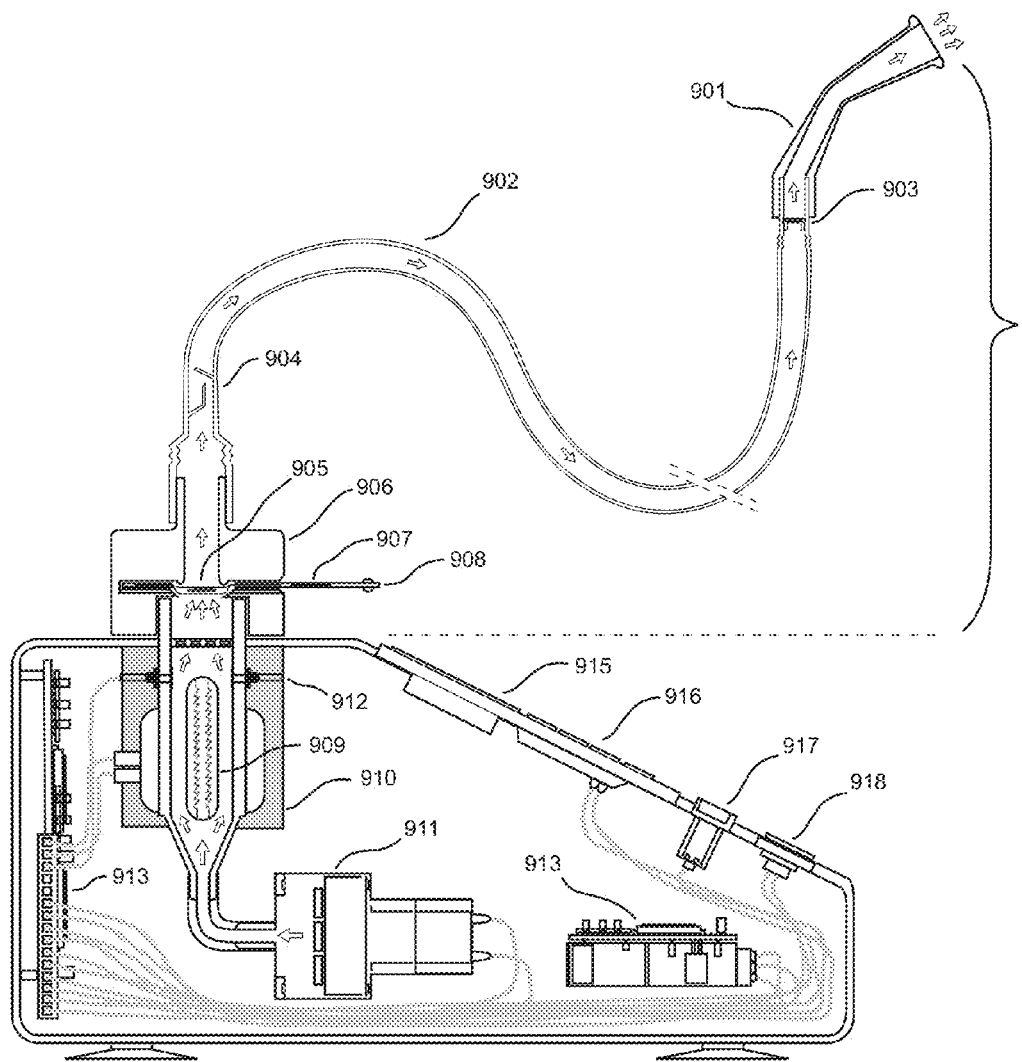
FIG. 11 depicts an alternate embodiment of a dose vaporizer

FIG. 11 depicts an alternative embodiment of a dose vaporizer. Removable vaporizer tube consists of disposable mouthpiece 901; disposable flexible hose 902; disposable expandable vapor reservoir 903; disposable one-way sanitary vapor valve 904: a dose 905 housed within a cartridge vaporization chamber 906. The cartridge may contain an RFID chip or other notification means (for example radio transmitter) and may also contain a means for detecting tampering with the cartridge 908. A heat source 909 heats up and vaporizes the dose 905 contained within the dose cartridge 908. Insulation 910 may optionally be used to isolate the heat source 909 from surrounding structures. An air pump 911 pushes air in the direction of the arrows indicated. Exhaust temperature and data sensors 912 measure the temperature and other physical/chemical characteristics of the vapor. The vapor itself is generated from heated air passing through a medical dose 905 of a vaporizable substance (in one embodiment, *cannabis*) held in place and surrounded by a dose suspension screen itself contained within a medical dose cartridge. Data recognition means (in one embodiment, an infrared-scannable barcode) may be located on the medical dose cartridge 906 so as to tracking and/or verifying use and user of the medical dose, and may, in one embodiment, be readable by medical dose/data connections. Separate intake temperature sensor data recorders and data connections may also be utilized, as well as a processor circuit board 914; LED display 915; data display keys 916; USB data port 917; and for warm-up switch 918. An insulation heat sink absorbs excess heat and keeps the starting temperature of the heated air utilized to generate the vapor fairly constant. In one embodiment, the air may itself be heated by a heat element and driven through the machine by an air flow fan.

Figure 12:
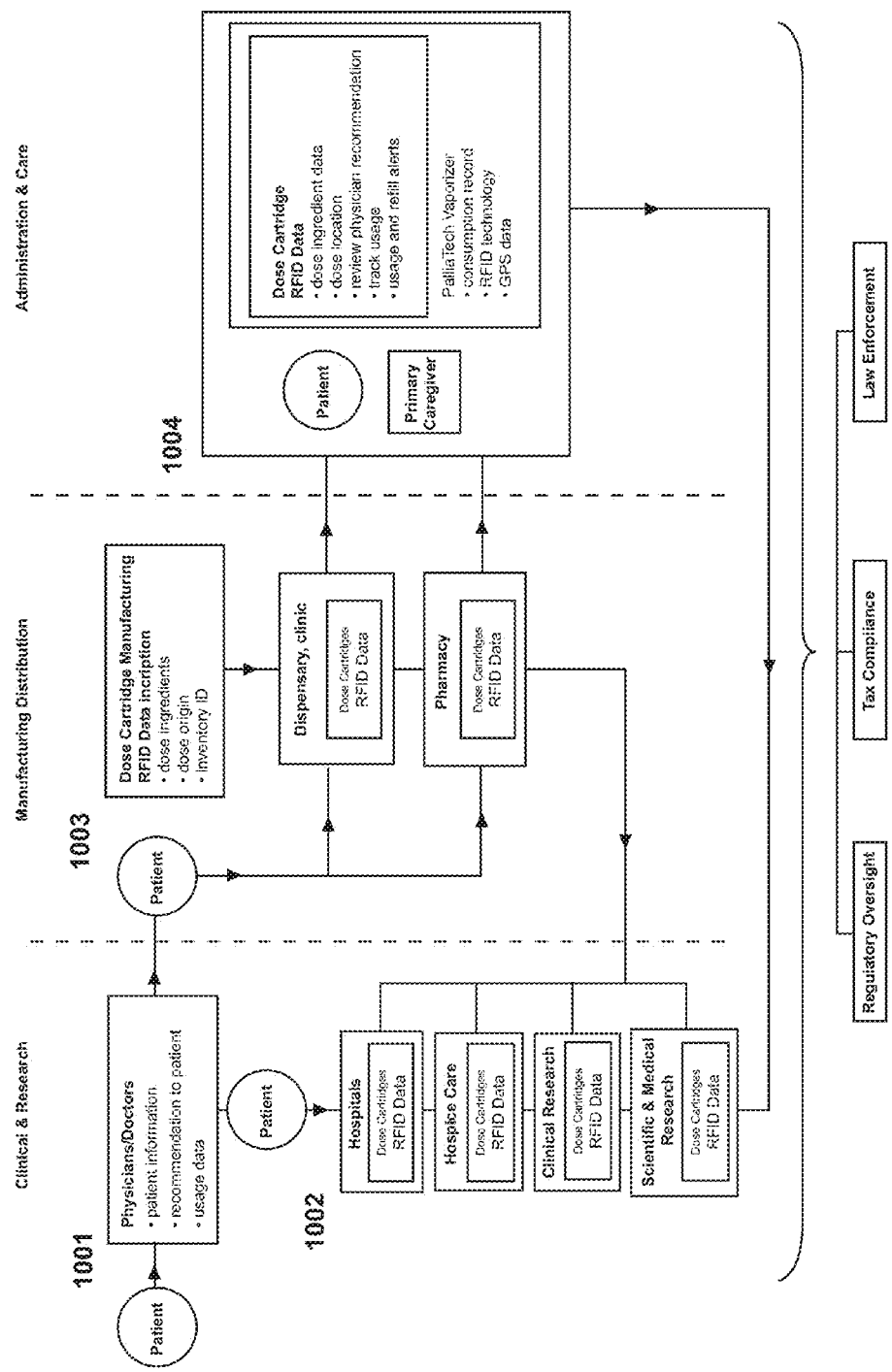
FIG. 12 depicts an embodiment of informatics employed by the systems, devices and/or methods described herein.

FIG. 12 depicts an alternative embodiment of a comprehensive medical solution comprised of purpose-built subsystems. The three subsystems may include a dose cartridge vaporizing system; a disposable safety/sterility system; and a clinical monitoring system. Physicians may gather information from a variety of sources (including the patient themselves) to determine whether the patient would benefit from a particular dosage of a product.) 1001. Subsequent to a physician determination, data related to the patient's individually identifiable information, condition, and prescribed use of a substance (in one example, *Cannabis*) may be provided 1002 to any of a hospital database, pharmacy database, hospice database, research database, law enforcement database, etc. Separately, dose cartridges containing a dose of a substance (in one embodiment, *Cannabis*) may be produced 1003 and "tagged" with any of a number of differing types of data, including identity of the dose; prescribed individual corresponding to the dose; batch and lot number of the dose; expiration date of the dose; usage of the dose; etc. Doses may be prescribed and/or distributed to a patient, and data related to machine usage; dose usage; patient usage, etc. may be stored in a database or provided in varying forms to any matter of healthcare provision, regulatory oversight, tax collection and/or law enforcement entities. 1004.

In another embodiment, any portion of the instant invention—including, but not limited to, the flexible tube, dose cartridge and/or mouthpiece—may be made disposable, individually sterilizable, separable from the main apparatus of the invention and/or reusable and/or returnable.

Dose Vaporizer

In one embodiment, the dose vaporizer provides a mild, non-noxious, and non-irritating vapor so as to facilitate administration of medical dose (in one embodiment, *cannabis*) vapors with a reduced incidence and/or risk of concomitant administration of carcinogens.

In another embodiment, the dose vaporizer provides a vapor dose that utilizes substantially all of the active ingredients within a particular medical (in one example, *cannabis*) sample, thus increasing efficiency of delivery of *cannabis* active ingredients.

In another embodiment, the instant dose vaporizer permits physicians to record and control frequency, time and date of use while enabling treatment to the dose-response curve of individual patients (a critical healthcare benefit). Doctors can deliver improved care due to patient ability to self-administer consistent doses with maximum efficiency (little waste) and efficacy (greater absorption of active ingredients). Tamper-resistant packaging and digital record-keeping offer states and law enforcement authorities new tools to help ensure accountability, control and transparency throughout the medical *cannabis* supply chain.

In another embodiment, the amount of material vaporized is not alterable by the end user.

In another embodiment, the flexible tube/mouthpiece may be removed while in operation, resulting in use of the dose vaporizer in a manner that provides the vaporizer stream into a given physical space, for example, a room of a house.

In another embodiment, the instant invention is designed exclusively for use by legally approved patients.

In another embodiment, the instant invention is designed for home use bedside or on any or all flat table top like surfaces that are suitable for such a device and able to withstand the level of heat that may be generated by sustained use.

In another the instant invention is designed for portable use, for example, as a backpack unit; a wheeled unit; a battery or liquid-fuel-powered unit.

In another embodiment, the instant invention is designed to be set at the specific temperature by the factory or the legally approved provider and or doctor or caregiver that is required to vaporize Medical *Cannabis* or a single specific temperature that is required to vaporize any and all other medications that have been legally prescribed.

In another embodiment, the instant invention is designed to be set to deliver any of a number of vaporizable medicines/alternative compounds, including but not limited to aromatherapy compounds and/or substrates.

In another embodiment, the instant invention is designed to have one and only one temperature setting activatable by the user.

In another embodiment, the instant invention is not designed to be used with more than one medical product.

In another embodiment, the temperature, time and air velocity settings of the instant invention are not variable.

In another embodiment, the instant invention is designed to have a baffle that will block the heat source and prevent the combustion of the material to be vaporized.

In another embodiment, the baffle system is designed to be set at a single temperature by the factory.

In another embodiment, the baffle system is designed to be activated by a time period set by the factory or controlled by the doctor.

In another embodiment, the baffle system is designed to be activated by a temperature set by the factory or controlled by the doctor.

In another embodiment, the heating element is designed to be activated by a time period set by the factory or controlled by the doctor.

In another embodiment, the heating element is designed to be activated by a temperature set by the factory or controlled by the doctor.

In another embodiment, the baffle is designed to be activated by a time or temperature set by the factory or controlled by the doctor so as to optimize heating and/or inhalation periods (for example in order to optimize extraction of the vapors from the sample) and/or for the purpose of avoiding combustion and/or control total amount of vapor/active ingredient taken in by the patient.

In one embodiment, the baffle system is designed and intended to provide a vaporizing heat stream at a temperature approximately 10 degrees below the combustion point of medical *cannabis*.

In another embodiment, the vaporizer is designed to deliver vapor to the lungs of legally approved patients via oral inhalation through a simple tube made from easily cleaned and sterilized materials such as plastic, glass, ceramics or low heat conducting metal.

In another embodiment, the instant invention's vaporizer carbureting holes are designed to allow cool air to rush into the delivery tube, behind the heated vapor at the time the baffles block off the heat source.

In another embodiment, the carbureting holes are designed to use cool air to push the heat created vapors deep into the patients' lungs for more effective absorption of the intended compounds of the vaporized material.

In another embodiment, the carbureting holes are designed to insure that the vapors cannot reach the patients body/lungs at temperatures that would create discomfort.

In another embodiment, the instant invention vaporizer is designed to only accept medical *cannabis* and any legally prescribed material that is packaged by a licensed provider in proprietary dose cartridges.

In another embodiment, use of standardized, optimized dose cartridges may facilitate consistent dosing amounts and efficacy by minimizing human error in the preparation and use of doses prepared by the user from "loose" or unprocessed vaporizable substances.

In another embodiment, the vaporizer is designed to record proper use and Illegal misuse or abuse with a data storage system.

In another embodiment, the vaporizer is designed to be used by one and only one legally approved patient at a time.

In another embodiment, the vaporizer is designed to be very simple to use by patients that have limiting or debilitating conditions.

In another embodiment, the vaporizer is designed to be impossible to use incorrectly with automatic "lockout" cutoff if misuse, dangerous temperature levels, illegal use and any or all unintended use is detected.

In one embodiment, a lockout is tied to use of a purpose-built machine in the wrong location, which may be ascertained, for example, by use of GPS geolocation.

In another embodiment, a lockout is tied to use of the machine at an improper temperature.

In another embodiment, a lockout is tied to use of the machine at an improper frequency of use.

In another embodiment, a lockout is tied to use of the machine utilizing an improper dose.

In another embodiment, a lockout is tied to use of the machine by an improper person.

In another embodiment, a lockout is tied to use of the machine with an improper material.

In another embodiment, the vaporizer is designed to eliminate the need for a legally approved patient to handle, come on contact with or otherwise contaminate, subdivide or transfer the material to be vaporized.

In another embodiment, the vaporizer is designed to electronically alert law enforcement, care givers, insurance providers and any or all legally authorized interested parties of both proper use and illegal misuse via the Internet, Wi-Fi, blue tooth, cellular phone, land line telephone, telegraph and or other means.

In another embodiment, the vaporizer is designed to fully extract the intended compounds of the material to be vaporized by proper and exact temp settings and controlling the volume of heated air that is allowed to pass through the material to be vaporized.

In another embodiment, the vaporizer is designed to "present" the proprietary dose cartridge to the heat source in the optimal way to insure complete vaporization of the material.

In another embodiment, the vaporizer is designed to completely vaporize each dose cartridge in a single patient use and record each used dose in a simple data collection system.

In another embodiment, the vaporizer is designed to detect the identity of the legally authorized user through methods that can include fingerprint sensors, retinal scanning, proprietary passwords and electric confirmation from the recommending physician, legally authorized care giver In another embodiment, the vaporizer is designed to work only with single-use dose cartridges, and will not accept a cartridge more than once even if the sample contained within is not fully vaporized.

In another embodiment, the instant invention is designed to avoid unintentional combustion through use of any or all of a smaller sample; limited temperature; limited airflow; and/or limited air intake.

In another embodiment, the heat source is programmed to maintain a precise temperature below the maximum temperature. in the event of a malfunction Temp. sensors between the heat source and the dose cartridge electronically trigger a baffle that blocks heat from substance before it exceeds the minimum temp necessary for the combustion of *cannabis*.

In another embodiment, the medical inhalation device includes a disposable vaporizer tube.

In another embodiment, the medical inhalation device includes a sterilizable vaporizer tube.

In another embodiment, the medical inhalation device includes a sterile vaporizer tube.

In another embodiment, the medical inhalation device further includes a one-way sanitary vapor valve.

Dose Vaporizer Cartridge

In one embodiment, the dose vaporizer cartridge is a new device that delivers a single dose of medicine (in one embodiment, *cannabis*) that has been produced for medicinal uses.

In another embodiment, the dose is encapsulated between two heat-resistant screens.

In another embodiment, the dose may be encapsulated between/wrapped within any available substrate, such as paper, plastic, mesh, metal, etc.

In another embodiment, the two heat-resistant screens are designed so as to assist in delivering equivalent heat to the entirety of the encapsulated sample when exposed to heated air and/or convection processes.

In another embodiment, the dose vaporizer cartridge is adapted and sized so as to be precisely fit into a dose vaporizer so as to provide for optimal vaporization of medical product encapsulated within the heat resistant screens.

In one embodiment, the dose vaporizer cartridges are refillable. In another embodiment, the dose vaporizer cartridges are reusable. In another embodiment, the dose vaporizer cartridges are tamper-resistant, and will not work when refilled by the end user. In another embodiment, the dose vaporizer cartridges are tamper-resistant, and will work only when refilled by an authorized dispenser, who may, without limitation, be a health-care provider.

In another embodiment, the dose cartridge allows physicians and/or third parties to create specific and/or customizable measured doses of medical *cannabis* that may be supplied within the dose cartridges. In one embodiment, such specific, controlled, measured doses of medical *cannabis* may include specific measured blends of multiple strains of *Cannabis* that are combined for the treatment of specific conditions and/or the packaging of measured amounts of a single strain of medical *cannabis*. In one embodiment, the dose cartridge is designed to deliver a specific amount of the chemicals in medical *cannabis* to the patient.

In one embodiment, the dose cartridge encapsulates *cannabis* or any and all other substances to be delivered through vaporization between two screens, pieces of mesh or otherwise suitable material.

In another embodiment, the dose cartridge is tamper evident and designed to clearly record and/or visually indicate misuse or attempted misuse.

In another embodiment, the cartridge is also labeled for easy identification by Pharmacists, doctors patients and all caregivers. The cartridge is designed to be easily handled by patients and caregivers.

In another embodiment, the cartridge is designed to only be used in a proprietary vaporizing delivery system.

In another embodiment, the dose cartridges are designed to be compatible with and/or usable with a variety of brands and models of vaporizers that are available and/or may become available in the marketplace.

In another embodiment, the cartridge is designed to be packaged in sterile easily identifiable boxes that can be distributed by pharmacies, doctors and any and all properly licensed caregivers or dispensaries whether traditional or automated.

In another embodiment, the cartridge facilitates use of a medical product (in one instance, *cannabis*) without requiring expensive and time-consuming pretreatment of the medical product by, for example, solubilizing, heating or otherwise transforming the medical product.

In another embodiment, the dose consists of sterilized *cannabis* or other material, for example through use of heat, ultraviolet, or gamma-ray sterilization.

Comprehensive Delivery System

In one embodiment, the instant invention is designed to track and control Medical *cannabis* and other controlled substances or drugs that can be vaporized from their growth or production through packaging and until final consumption by the legally intended patient.

In one embodiment, such tracking can be facilitated by use of any of a number of available technologies, such as RFID; Internet access; wireless access; USB device monitoring; smartphone application; internet connection; social media; etc.

In another embodiment, the instant invention is designed to collect, organize, analyze and provide accurate and precise information about the use of medical *cannabis* by legally authorized patients to legally authorized interested parties including, without limitation, doctors, medical researchers, patient advocates, politicians, patients, insurance providers, state governments, and government agencies.

In another embodiment, the instant invention is designed to detect any or all illegal use, abuse, subdivision, and unauthorized redistribution of the materials packaged in proprietary dose cartridges for use in a proprietary vaporizer. The instant invention is designed to create and utilize a single dose/single use package for medical *Cannabis*.

In another embodiment, the instant invention is designed to record the precise time and location that a legally authorized patient ingests medical *Cannabis* utilizing simple data recording software and/or a GPS location device; and cross-verifying barcode/RFID using an available database or other reporting/recording methods described above.

In another embodiment, the instant invention is designed to rapidly and efficiently deliver the beneficial effects of medical *cannabis* to legally authorized patients.

In another embodiment, the instant invention is designed to completely utilize and eliminate the waste of the materials including medical *cannabis* that is packaged in a proprietary dose cartridge and vaporized with a proprietary vaporizer.

In another embodiment, the instant invention is designed to eliminate direct contact by legally authorized patients with the material packaged in proprietary dose cartridges.

In another embodiment, the instant invention is designed to track a plurality of individually-packaged doses, including tracking the identity of the person utilizing the dose; receiving the dose; purchasing the dose; ascertaining whether the dose was completely administered; and ascertaining whether the dose cartridge was tampered with and/or refilled.

In another embodiment, the instant invention is usable for tracking individual acquisition and use of doses, regardless of whether the individuals are located within a healthcare facility.

In another embodiment, the instant invention is capable of tracking dispensation and use of a product through its full life cycle; e.g. assessing when the relevant active ingredients have been substantially vaporized and delivered from the dose cartridge.

In another embodiment, the instant invention assesses use of a dose through non-visual means. In another embodiment, such non-visible means are, for example, through use of test strips and/or chemical assays. In another embodiment, such non-visible means are indirect measurements, for example, the measurement of heat setpoint obtained and duration of heat setpoint obtained at the mouthpiece (downstream of vaporization) as a method of indirectly measuring extent of vaporization and incidence of combustion of the medical sample.

While a number of embodiments of the present invention have been described, it is understood that these embodiments are illustrative only, and not restrictive, and that many modifications and/or alternative embodiments may become apparent to those of ordinary skill in the art. For example, any steps may be performed in any desired order (and any desired steps may be added and/or any desired steps may be deleted). Therefore, it will be understood that the appended claims are intended to cover all such modifications and embodiments that come within the spirit and scope of the present invention.

What is claimed is:

1. A medical inhalation system, comprising:
   a medical inhalation device for the delivery of a dose of medical *Cannabis*, including a housing having an inlet for receiving air from an external environment and introducing the air into the housing, a vaporization chamber, a heat source for heating the air to provide heated air and to provide heat to the vaporization chamber, a baffle, and an outlet in communication with the vaporization chamber;
   a dose cartridge including the dose of medical *Cannabis*, and
   a temperature sensor located between the heat source and the dose cartridge,
   wherein the dose cartridge is sized and shaped to be inserted into the vaporization chamber of the medical inhalation device,
   wherein when the dose cartridge is inserted into the vaporization chamber of the medical inhalation device, the heat source is adapted to heat the dose of medical *Cannabis* to a delivery temperature by the heated air within the vaporization chamber for a heating time period to produce therapeutically-active ingredients from the dose of medical *Cannabis*,
   wherein the medical inhalation device is adapted to maintain the delivery temperature of the dose of medical *Cannabis* of the inserted dose cartridge within the vaporization chamber for a time period prior to the delivery of a vaporized form of the therapeutically-active ingredients from the dose of medical *Cannabis* through the outlet,
   wherein the inserted dose cartridge is constantly maintained within the vaporization chamber of the medical inhalation device during the delivery of the vaporized form of the therapeutically-active ingredients of the dose of medical *Cannabis* for a plurality of inhalations, and that the delivery temperature of the dose of medical *Cannabis* is maintained within a predetermined temperature range during the delivery of the vaporized form of the therapeutically-active ingredients of the dose of medical *Cannabis* , and
   wherein the temperature sensor is adapted to electronically trigger the baffle to block heated air to the dose cartridge before the temperature of the heat exceeds the minimum temperature of combustion of the dose of medical *Cannabis*.

2. The medical inhalation system of 1, wherein the vaporization chamber is closed when the dose of medical *Cannabis* is heated.

3. The medical inhalation system of 1, further comprising a control system for measuring, controlling and maintaining the temperature of the heated air.

4. The medical inhalation system of claim 3, wherein the control system controls the heating time period.

5. The medical inhalation system of claim 3, wherein the control system further controls the volume of the heated air passing through the dose of medical *Cannabis*.

6. The medical inhalation system of claim 3, wherein the control system includes a vapor data sensor and a vapor data recorder.

7. The medical inhalation system of 1, wherein a flow of the heated air is controlled by a pump located within the housing.

8. The medical inhalation system of claim 1, further comprising a control system for determining authorized use of the dose of medical *Cannabis* with the medical inhalation device.

9. The medical inhalation system of claim 8, wherein the control system queries a database to match the dose of medical *Cannabis* with user, usage and product data.

10. The medical inhalation system of claim 8, wherein the control system queries a database to match the dose cartridge containing the dose of medical *Cannabis* with the authorized medical inhalation device, wherein the control system is capable of locking out the medical inhalation device when the dose cartridge is not authorized for use with the device, and wherein the control system locks out the medical inhalation device when a frequency of use of the device exceeds a usage limit.

11. The medical inhalation system of claim 8, wherein the control system is capable of locking out the medical inhalation device when biometric identification of a user does not match an identity of an authorized user of the medical inhalation device.

12. The medical inhalation system of claim 8, wherein the control system locks out the medical inhalation device when the system detects evidence of tampering or alteration of the inserted dose cartridge.

13. The medical inhalation system of claim 8, wherein the control system locks out the medical inhalation device when the dose cartridge is not authorized for use at a particular location.

14. The medical inhalation system of claim 8, wherein the dose cartridge includes dose cartridge data.

15. The medical inhalation system of claim 14, wherein the dose of medical *Cannabis* is a single, measured unit.

16. The medical inhalation system of claim 15, wherein the dose cartridge includes a screen positioned within the dose housing, and wherein the dose of medical *Cannabis* is encapsulated by the screen.

17. The medical inhalation system of claim 1, further comprising a recorder for recording usage data relating to the use of the medical inhalation device and the dose of medical *Cannabis*.

* * * * *